US010905569B2

(12) United States Patent
Park et al.

(10) Patent No.: US 10,905,569 B2
(45) Date of Patent: Feb. 2, 2021

(54) METHOD AND SYSTEM FOR MANUFACTURING CUSTOMIZED BREAST PROSTHESIS, COMPUTER PROGRAM AND COMPUTER-READABLE RECORD MEDIUM FOR SAME, CUSTOMIZED BREAST PROSTHESIS, AND CUSTOMIZED CORRECTION BRASSIERE

(71) Applicant: Research Cooperation Foundation of Yeungnam University, Gyeongsangbuk-do (KR)

(72) Inventors: Soonjee Park, Gyeongsangbuk-do (KR); Jung Eun Lee, Daegu (KR); Su Hyeong Seong, Daegu (KR); Manseok Kim, Gyeongsangbuk-do (KR)

(73) Assignee: Research Cooperation Foundation of Yeungnam University

( * ) Notice: Subject to any disclaimer, the term of this patent is extended or adjusted under 35 U.S.C. 154(b) by 140 days.

(21) Appl. No.: 16/170,792

(22) Filed: Oct. 25, 2018

(65) Prior Publication Data

US 2019/0125549 A1    May 2, 2019

(30) Foreign Application Priority Data

Oct. 26, 2017    (KR) .......................... 10-2017-0140303

(51) Int. Cl.
*A61F 2/52* (2006.01)
*A61F 2/12* (2006.01)
*A61F 2/50* (2006.01)
*A61B 5/00* (2006.01)
*A61B 5/107* (2006.01)
*A41C 3/14* (2006.01)
*A41H 1/04* (2006.01)

(52) U.S. Cl.
CPC .......... *A61F 2/5046* (2013.01); *A61B 5/0077* (2013.01); *A61B 5/1077* (2013.01); *A61B 5/4312* (2013.01); *A61F 2/52* (2013.01); *A41C 3/148* (2013.01); *A41H 1/04* (2013.01); *A61F 2002/505* (2013.01); *A61F 2002/5056* (2013.01); *A61F 2002/523* (2013.01)

(58) Field of Classification Search
CPC .................................. A61F 2/12; A61F 2/52
USPC ........................................................ 623/7–8
See application file for complete search history.

(56) References Cited

U.S. PATENT DOCUMENTS

| | | | | |
|---|---|---|---|---|
| 6,544,100 | B1* | 4/2003 | Nadsady | A41C 3/144 450/38 |
| 6,755,861 | B2* | 6/2004 | Nakao | A61F 2/12 623/7 |
| 7,058,439 | B2* | 6/2006 | Eaton | A61F 2/52 600/425 |

(Continued)

*Primary Examiner* — Suzette J Gherbi
(74) *Attorney, Agent, or Firm* — Mendelsohn Dunleavy, P.C.

(57) ABSTRACT

The present invention provides a method of manufacturing a customized breast prosthesis in such a manner as to perform three-dimensional scanning of user's body and apply the same shape, the same volume, and the same density as the actual breast to have the same weight, a system for manufacturing the same, a computer program and computer-readable record medium for the same, a customized breast prosthesis manufacture by the above method, and a customized correction brassiere for accommodating the customized breast prosthesis.

12 Claims, 12 Drawing Sheets

(56) References Cited

U.S. PATENT DOCUMENTS

| | | | |
|---|---|---|---|
| RE40,487 E * | 9/2008 | Eaton | A61F 2/52 264/222 |
| 2003/0074084 A1 * | 4/2003 | Nakao | A61F 2/12 623/23.67 |
| 2003/0208269 A1 * | 11/2003 | Eaton | A61F 2/52 623/7 |
| 2011/0317890 A1 * | 12/2011 | Baroni | G06T 17/00 382/128 |
| 2012/0130490 A1 * | 5/2012 | Erni | A61F 2/12 623/8 |
| 2019/0321065 A1 * | 10/2019 | Yilmaz | A61B 6/466 |
| 2020/0060356 A1 * | 2/2020 | Trangmar | A41C 3/142 |
| 2020/0134930 A1 * | 4/2020 | Oommen | A41H 1/00 |
| 2020/0178936 A1 * | 6/2020 | Padwal | G06T 7/0012 |
| 2020/0242686 A1 * | 7/2020 | Garcia Giraldez | G06Q 30/0269 |

* cited by examiner

DRAWINGS

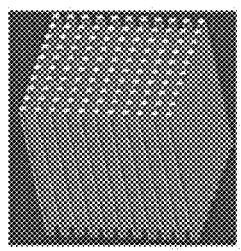
FIG. 7A1
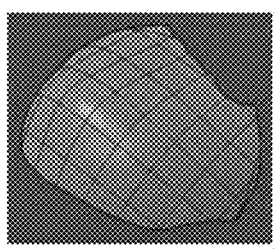
FIG. 7B1
FIG. 7C1
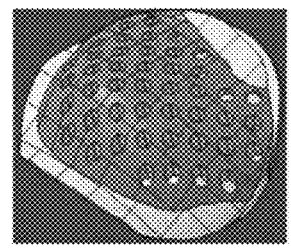
FIG. 7D1
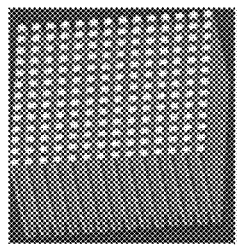
FIG. 7A2
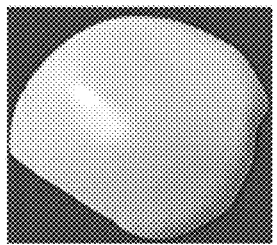
FIG. 7B2
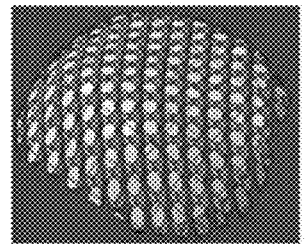
FIG. 7C2
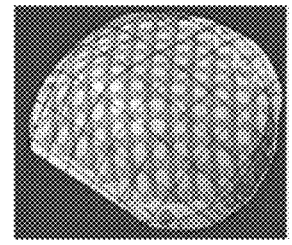
FIG. 7D2

 filled inside shape
 emptied inside shape
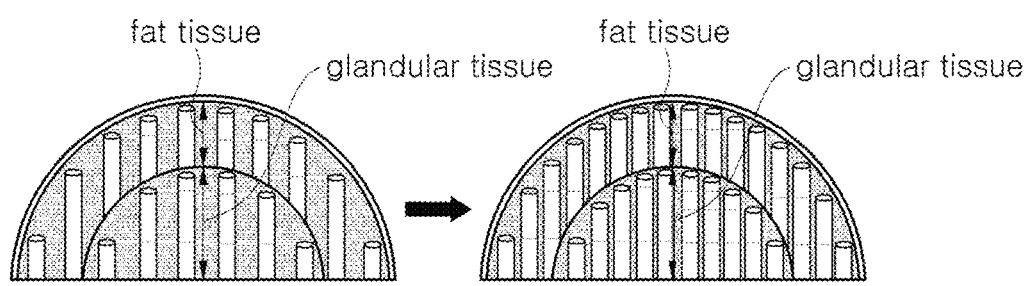
FIG. 8A          FIG. 8B

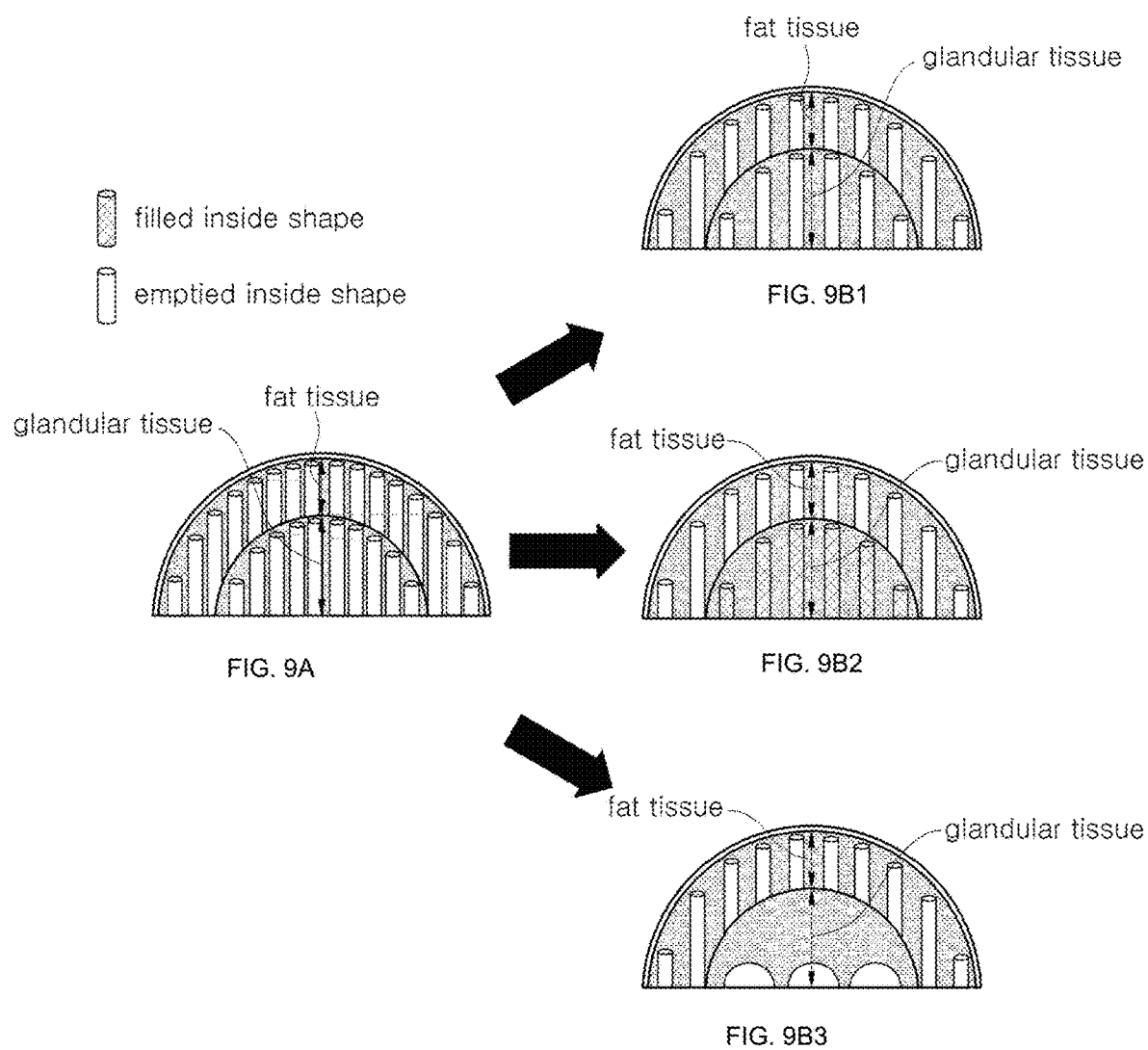

METHOD AND SYSTEM FOR MANUFACTURING CUSTOMIZED BREAST PROSTHESIS, COMPUTER PROGRAM AND COMPUTER-READABLE RECORD MEDIUM FOR SAME, CUSTOMIZED BREAST PROSTHESIS, AND CUSTOMIZED CORRECTION BRASSIERE

CROSS REFERENCE TO RELATED APPLICATION

The present application claims priority to Korean Patent Application No. 10-2017-0140303, filed on Oct. 26, 2017, the entire contents of which is incorporated herein for all purposes by this reference.

BACKGROUND OF THE INVENTION

Field of the Invention

The present invention relates to a breast prosthesis and a correction brassiere for a mastectomy patient and, more particularly, to a method and a system for manufacturing a customized breast prosthesis, a computer program and computer-readable record medium for the same, a customized breast prosthesis, and a customized correction brassiere for a mastectomy patient using a 3D scanning device and a 3D printing device.

Description of the Related Art

In the case of patients with mastectomy, a sense of loss due to damage to the body part, a sense of shame, and the like are caused and furthermore a feeling of self-esteem is reduced. In addition, due to the horizontal imbalance of the human body, heights of the shoulder and shoulder blade of the surgical site are increased, the back is bent, and the muscle is contracted, thereby causing suffering from postural distortion and the pain due to poor posture.

Although an increase in breast cancer incidence and survival rate has led to an increase in breast cancer survivors in Korea, a breast prosthesis or a correction brassiere for patients with mastectomy is dependent on a foreign technology.

The prosthesis that is commercially available in the related art has problems of weight imbalance, a sensation of a foreign body, and postural distortion in the future even if the shape thereof is similar to that of actual breast because the density of the prosthesis is different from each other in whole or in part from that of actual breast.

In recent years, the service of creating a breast prosthesis using a cast method has been provided through foreign internet sites, but generalization thereof is limited in that the service has to be performed in such a manner as to be contacted with sensitive body part and is very expensive.

International Patent Application Publication No. WO 2016/022729 in the related art discloses a 3D-printed unibody mesh structure for breast prosthesis and a method of making the same. Described herein is a breast prosthesis, including an inner wall mesh, an outer wall mesh, a band, etc., having different densities. However, it does not provide a method of optimizing the shape, volume, and weight of the breast prosthesis in such a manner to achieve the balance with the actual lost breast or normal breast of the user.

Thus, there is an increased need for a breast prosthesis that applies the same shape, the same volume, and the same density as the normal breast to have the same weight.

SUMMARY OF THE INVENTION

Accordingly, the present invention has been made keeping in mind the above problems occurring in the related art, and an object of the present invention is to provide a method of manufacturing a customized breast prosthesis in such a manner as to perform three-dimensional scanning of user's body and apply the same shape, the same volume, and the same density as the actual breast to have the same weight.

It is also a further object of the present invention to provide a system for performing the method of manufacturing the customized breast prosthesis, a computer program and computer-readable record medium for the same, a customized breast prosthesis manufactured through the method, and a customized correction brassiere for accommodating the same.

In order to obtain the above objects, according to an aspect of the present invention, the present invention provides a method of manufacturing a customized breast prosthesis performed by a system for manufacturing the customized breast prosthesis. The method of manufacturing a customized breast prosthesis includes performing three-dimensional scanning of a user's body; acquiring shape, volume, and weight data of a resected breast part; selecting a material of the breast prosthesis; designing the customized breast prosthesis that is adjusted to the shape, volume, and weight of the resected breast part with the selected material of the breast prosthesis.

Herein, the acquiring of the shape, volume, and weight data of the resected breast part may include determining whether the shape, volume, and weight data of the resected breast part are acquired or not, and when the shape, volume, and weight data of the resected breast part are not acquired, further include modeling a curved surface of the resected breast part; calculating the volume of the resected breast part using the curved surface of the modeled resected breast part; and calculating the weight of the resected breast part from the volume of the resected breast part.

Herein, the modeling of the curved surface of the resected breast part may include modeling a curved surface of a normal breast part from the scanned data; moving the modeled curved surface of the normal breast part in a horizontally symmetrical manner on the basis of a breast center line; and modeling the curved surface of the resected breast part by connecting the normal breast part moved in the horizontally symmetrical manner to a user surface of a breast resected region.

Herein, the calculating of the volume of the resected breast part may include creating a boundary of a glandular tissue dominant layer and a fat tissue dominant layer in the curved surface model of the resected breast part to complete the glandular tissue dominant layer; removing the glandular tissue dominant layer from the curved surface model of the resected breast part to complete the fat tissue dominant layer; and calculating each of a volume of the glandular tissue dominant layer and a volume of the fat tissue dominant layer.

Herein, the calculating of the volume of the resected breast part may include calculating the weight of the resected breast part from a regression equation between a volume and a weight of the breast; calculating a target weight of the glandular tissue dominant layer using a volume of the glandular tissue dominant layer and a density of glandular tissue, or calculating a target weight of the fat tissue dominant layer using a volume of the fat tissue dominant layer and a density of fat tissue; calculating the target weight of the fat tissue dominant layer by subtracting the target weight of the glandular tissue dominant layer from the weight of the resected breast part, or calculating the target weight of the glandular tissue dominant layer by subtracting the target weight of the fat tissue dominant layer from the weight of the resected breast part.

Herein, the designing of the customized breast prosthesis may be performed by applying inside shapes to each of the glandular tissue dominant layer and the fat tissue dominant layer to adjust the target weight of the glandular tissue dominant layer and the target weight of the fat tissue dominant layer while maintaining a form of each of the glandular tissue dominant layer and the fat tissue dominant layer with the selected material.

In addition, the method of manufacturing a customized breast prosthesis may be provided so that for the application of the inside shapes, a reduction weight or an addition weight of the glandular tissue dominant layer is calculated using an equation below to adjust the target weight of the glandular tissue dominant layer, $$\Delta W_G = (V_G \times \rho) - W_{TG}$$

($W_{TG}$: target weight of glandular tissue dominant layer, $\rho$: material density, $V_G$: volume of glandular tissue dominant layer, $\Delta W_G$: reduction (+) weight or addition (−) weight of glandular tissue dominant layer), and a reduction weight or an addition weight of the fat tissue dominant layer is calculated using an equation below to adjust the target weight of the fat tissue dominant layer, $$\Delta W_F = (V_F \times \rho) - W_{TF}$$

($W_{TF}$: target weight of fat tissue dominant layer, $\rho$: material density, $V_F$: volume of fat tissue dominant layer, $\Delta WF$: reduction (+) weight or addition (−) weight of fat tissue dominant layer)

In addition, the method of manufacturing a customized breast prosthesis may be provided so that the breast prosthesis is designed by forming the inside shapes with voids when it is necessary to reduce the weight to adjust the target weight for each layer, and the breast prosthesis is designed by forming the inside shapes with a material having a density higher than that of a material of the breast prosthesis when it is necessary to add the weight to adjust the target weight.

In addition, the method of manufacturing a customized breast prosthesis may be provided so that a distance between the inside shapes is adjusted to adjust the target weight until a difference between the designed breast prosthesis weight and the target weight is within an allowable tolerance.

The method of manufacturing a customized breast prosthesis may further include performing 3D printing of the designed customized breast prosthesis upon the selected material of the breast prosthesis.

According to another aspect of the present invention, the present invention provides a customized breast prosthesis manufactured by the method mentioned above.

According to another aspect of the present invention, the present invention provides a customized correction brassiere manufactured on the basis of creational design pattern using three-dimensional scanned data of a user's body to accommodate the customized breast prosthesis. The customized correction brassiere includes a patch type cup having a top cup and a bottom cup separated from each other; an upper extension of mesh material extended to an upper edge of the top cup; a left and right extension extended to both sides of the patch type cup; a support formed with a panel of a stretchable material positioned inside the patch type cup; an under portion connected to a lower portion of the patch type cup and having a lower side tape of a height of 2 cm or more; a U-shaped wing connected to left and right sides of the under portion; and a shoulder patch connected to the U-shaped wing and having a width of 2 cm or more.

According to another aspect of the present invention, the present invention provides a computer program stored on a computer readable recording medium to execute the method mentioned above.

According to another aspect of the present invention, the present invention provides a computer readable recording medium storing the computer program.

According to another aspect of the present invention, the present invention provides a system for manufacturing a customized breast prosthesis. The system includes a 3D scanning device scanning a user's body; a processing device acquiring shape, volume, and weight data of a resected breast part, selecting a material of the breast prosthesis, and designing the customized breast prosthesis that is adjusted to the shape, volume, and weight of the resected breast part with the selected material of the breast prosthesis; and a 3D printing device performing 3D printing of the designed customized breast prosthesis upon the selected material of the breast prosthesis.

According to the method of manufacturing a customized breast prosthesis and the customized breast prosthesis manufactured through the method of the present invention, it is possible to perform three dimensional scanning of user's body and apply the same shape, the same volume, and the same density as the actual breast to manufacture the breast prosthesis having the same weight, thereby preventing a loss of self-esteem due to damage to the user's body part.

In addition, it is possible to prevent the phenomenon that the heights of shoulder and shoulder blade of the surgical site are increased, the back is bent, and the muscle is contracted, due to the horizontal imbalance of the body, thereby causing suffering from postural distortion, the pain due to poor posture, and so on.

In addition, a manufacturing system for performing the method of manufacturing the customized breast prosthesis of the present invention, and a computer program and computer-readable record medium for the same enables a manufacturer to easily manufacture the customized breast prosthesis that is suitable for each user.

In addition, the customized correction brassiere for accommodating the customized breast prosthesis can provide the customized brassier having design, fitness, corrective effect, functionality, and comfortability for each individual user by manufacturing the pattern using the three-dimensional scanned data of the user's body.

BRIEF DESCRIPTION OF THE DRAWINGS

The above and other objects, features, and other advantages of the present invention will be more clearly understood from the following:

FIGS. 7A1 to 7D1 and 7A2 to 7D2 are views illustrating a step for designing a customized breast prosthesis in which inside shapes are formed of voids according to a preferred embodiment of the present invention;

FIGS. 8A and 8B illustrate a method of reducing the weight of a customized breast prosthesis in which inside shapes are formed of voids according to a preferred embodiment of the present invention;

FIG. 9A and FIGS. 9B1. 9B2 and 9B3 illustrate a method of increasing the weight of a customized breast prosthesis in which inside shapes are formed of voids according to a preferred embodiment of the present invention;

DETAILED DESCRIPTION OF THE INVENTION

Figure 1:
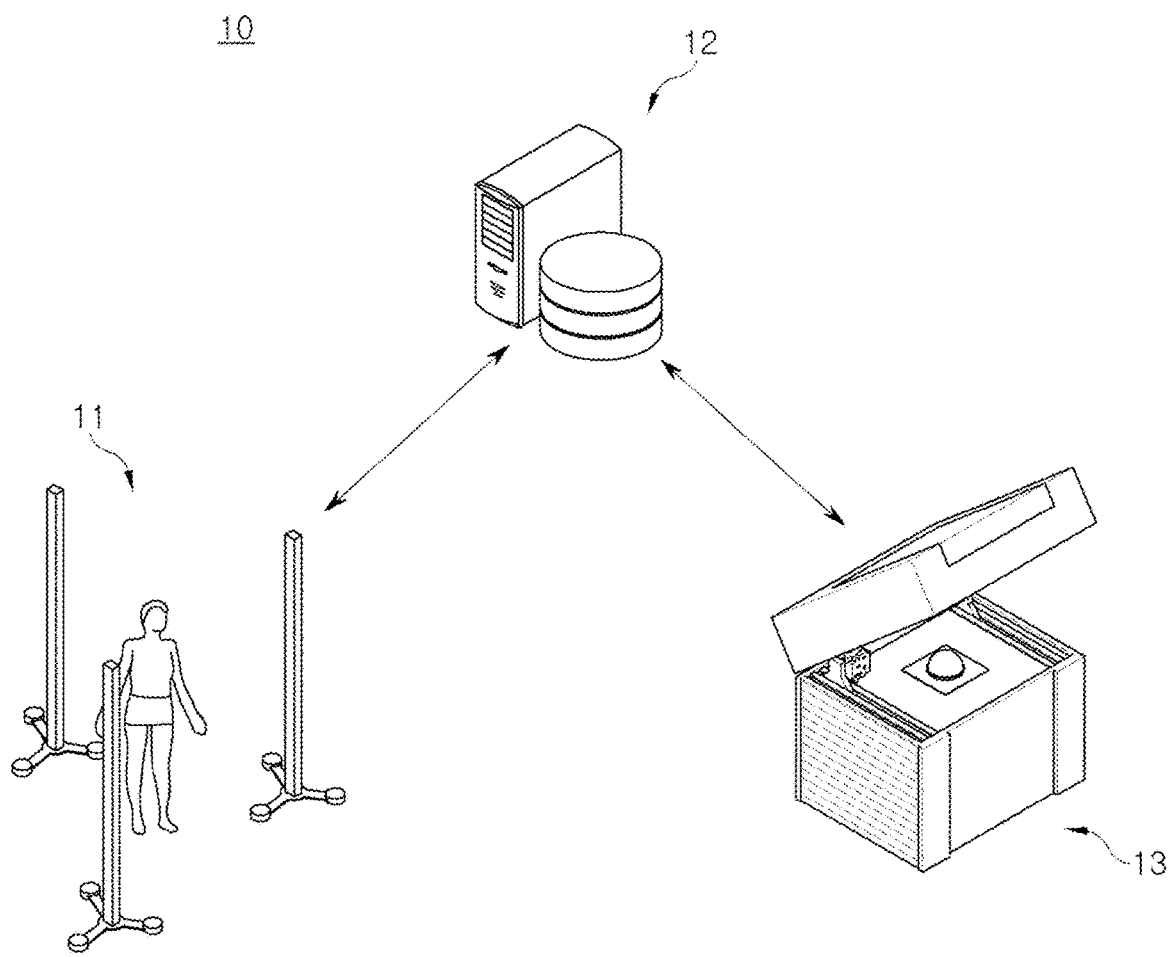
FIG. 1 is a schematic view illustrating a system for manufacturing a breast prosthesis according to a preferred embodiment of the present invention.

Reference will now be made in detail to embodiments of the present invention, examples of which are illustrated in the accompanying drawings, wherein like reference numerals refer to the like elements throughout and the overlapping description thereof will be omitted.

Although only a method of manufacturing the breast prosthesis is described in this specification, the same manufacturing method may be applied to manufacturing the prosthesis for another living tissue.

FIG. 1 is a schematic view illustrating a system for manufacturing a breast prosthesis according to a preferred embodiment of the present invention. Referring to FIG. 1, a manufacturing system 10 includes a three-dimensional scanning device 11 for scanning a user's body, a processing device 12 for receiving the scanned data to model a customized breast prosthesis, and a three-dimensional printing device 13 for printing the customized breast prosthesis.

The three-dimensional scanning device 11 is a device capable of scanning a human body of a user standing at a scanning position therein, for example, a three-dimensional scanner.

The data scanned by the three-dimensional scanning device 11 is transferred to the processing device 12.

The processing device 12 is a computing device such as PC, desktop, notebook, a tablet, a PDA, and the like in which program is executed, in such a manner as to cause the three-dimensional scanning device 11 to scan a user, model a customized breast prosthesis with the scanned data, and print the customized breast prosthesis using the 3D printing device 13.

The processing device 12 is connected to the three-dimensional scanning device 11 and the three-dimensional printing device 13 via a wired or wireless communication link.

In the processing device 12, the shape, volume, and weight of the resected breast part on the scanned data are acquired in such a manner as to be input directly from the user or be calculated from the scanned data. In addition, when the user selects a material for the breast prosthesis, the processing device designs to structure the breast prosthesis optimized for the shape, volume, and weight of the resected breast part for the selected material.

In the three-dimensional printing device 13, the breast prosthesis model designed by the processing device 12 is printed on a material such as silicon.

Figure 2:
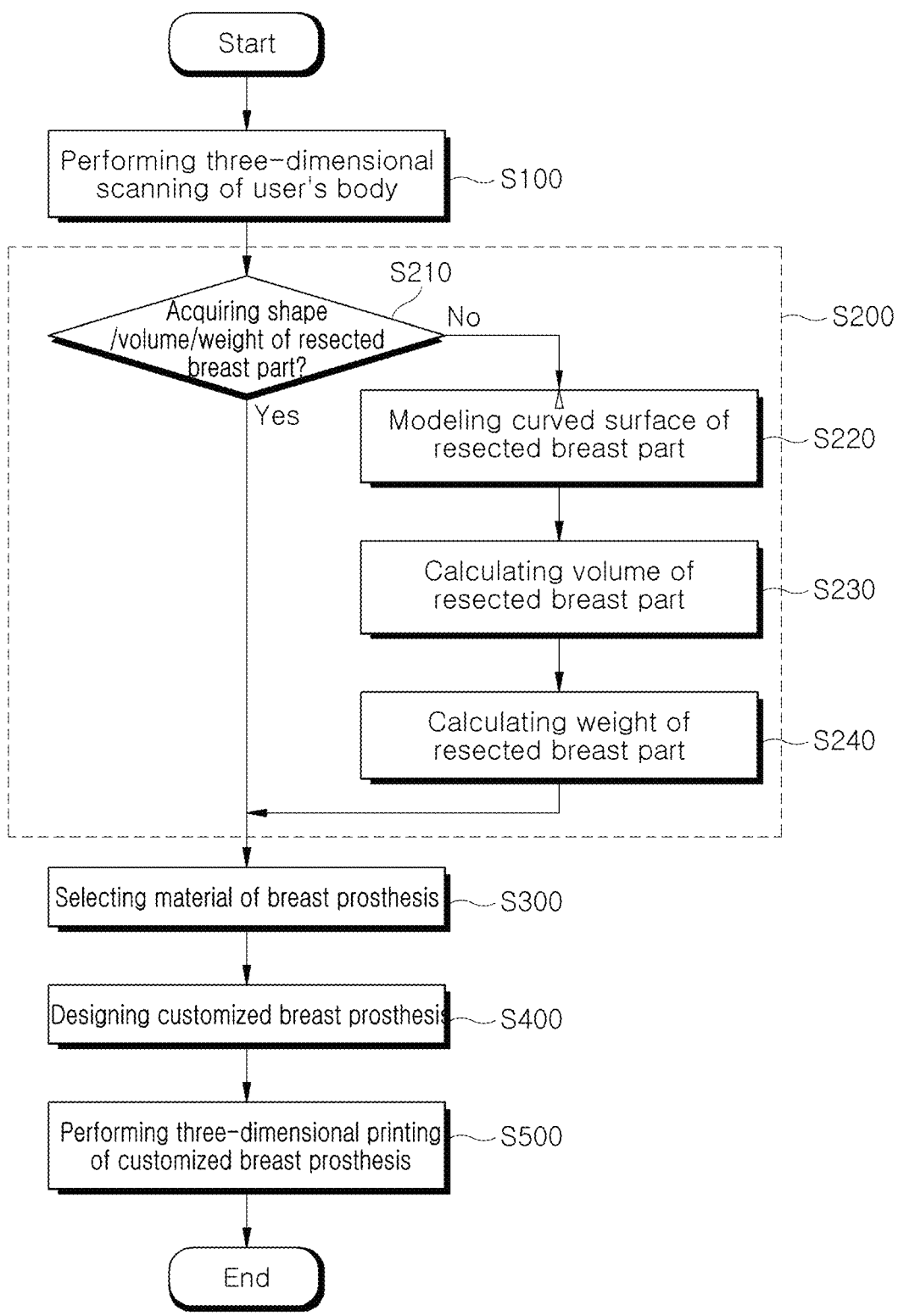
FIG. 2 is a flow chart illustrating a method of manufacturing a customized breast prosthesis according to a preferred embodiment of the present invention.

FIG. 2 is a flow chart illustrating a method of manufacturing a customized breast prosthesis according to a preferred embodiment of the present invention. Referring to FIG. 2, a method of manufacturing a customized breast prosthesis is performed by the manufacturing system 10, and includes a step of performing three-dimensional scanning of a user's body (S100), acquiring the shape, volume, and weight of the resected breast part (S200), a step of selecting a material of the breast prosthesis (S300), a step of designing a customized breast prosthesis (S400), and a step of performing three-dimensional printing of the designed customized breast prosthesis (S500).

In step of performing three-dimensional scanning of the user's body (S100), the user's body including both the normal breast and the resected breast is scanned using the 3D scanning device 11 such as a 3D human body scanner. This step (S100) also includes a step of allowing the user to make a preparation for 3D scanning.

For example, a medical tape may be used to lift the user's breast slightly just like wearing the brassiere in order to compensate for the overlapping of the lower chest due to mastoptosis during the scanning.

In addition, reference point marking members (for example, a sticker, a cone, etc.) may be attached to an upper edge point (uppermost point), a lower edge point (lowest point), an inner edge point (innermost point), and an outer edge point (outermost point) of user's breast outline. When performing 3D scanning after attaching such marking members, it is possible to clearly identify the outline of the breast from the scanning data.

In addition, the user takes a posture so that she allows her arms to be held at a distance (for example, 20 cm) slightly apart from her torso with spreading her arms, in order to acquire shape information of the underarm region within a range that does not change the body surface of other parts of the user's body.

Next, the step of acquiring the shape, volume, and weight of the resected breast part (S200) includes a step of determining whether or not to acquire the shape, volume, and weight data of the resected breast part (S210), and further includes a step of modeling a curved surface of the resected breast part (S220), a step of calculating the volume of the resected breast part (S230), and a step of calculating the weight of the resected breast part (S240), when the shape, volume, and weight data of the resected breast part are not acquired.

The step of determining whether or not to acquire the shape, volume, and weight data of the resected breast part (S210) is performed by determining whether the shape, volume, and weight data of the actual resected breast part have been acquired.

When the actual shape, volume, and weight data of the resected breast part are acquired, these data are used to design the customized breast prosthesis. Conversely, when the shape, volume, and weight data of the actual resected breast part are not acquired, the step of modeling the curved surface of the resected breast part S220, a step of calculating the volume of the resected breast part S230, (S240), and a step of computing the weight of the resected breast part (S240) are performed.

Figure 3:
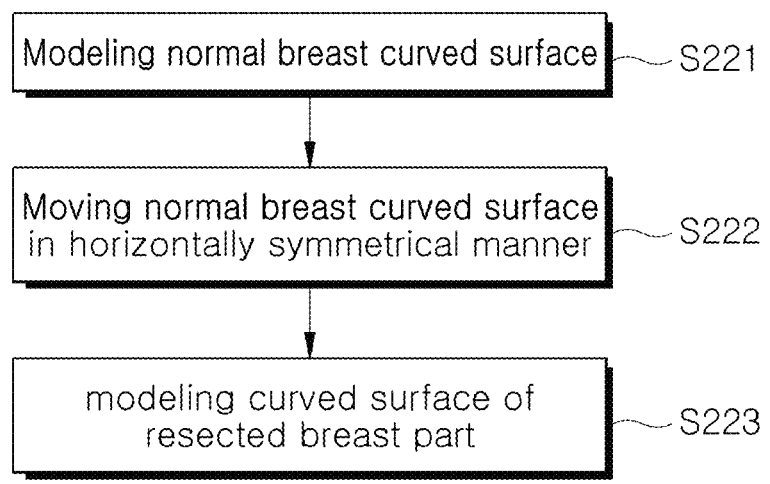
FIG. 3 is a detailed flowchart illustrating steps of modeling a curved surface of a resected breast part according to a preferred embodiment of the present invention.

The step of modeling the curved surface of the resected breast part (S220) includes a step of modeling the normal breast curved surface from the scanned data (S221), a step of moving the normal breast curved surface in a horizontally symmetrical manner (S222), and a step of modeling the curved surface of the resected breast part (S223), as shown in FIG. 3.

In the step of modeling the normal breast curved surface (S221), a breast part is first extracted from the 3D scan data. Then, the breast part is modeled with a curved surface by generating mesh data of the normal breast. A curve is formed along the marking members attached when scanning the human body at the region modeled with the curved surface. The created curve is extracted as an outer boundary to create a normal breast curved surface.

Next, in the step of moving the normal breast curved surface in a horizontally symmetrical manner (S222), the normal breast curved surface is moved in a horizontally symmetrical manner on the basis of the breast center line of the three-dimensional scanning data.

Next, the step of modeling the curved surface of the resected breast part (S223) is performed by connecting the normal breast curved surface moved in a horizontally symmetrical manner to a user surface of the resected breast part.

Figure 4A:
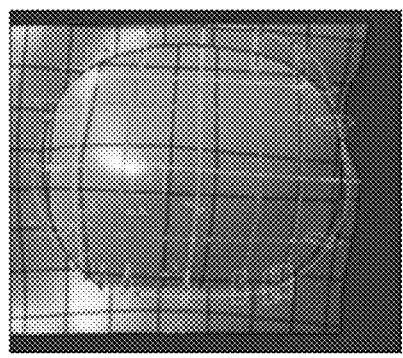
FIGS. 4A to 4C are views illustrating a step of modeling a curved surface of a resected breast part according to a preferred embodiment of the present invention.
Figure 4B:
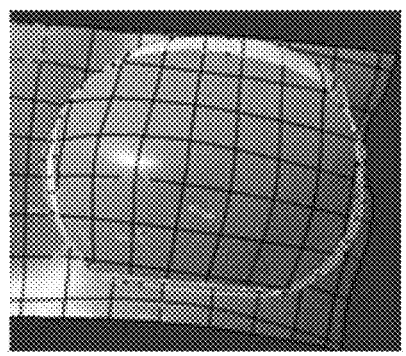
Figure 4C:
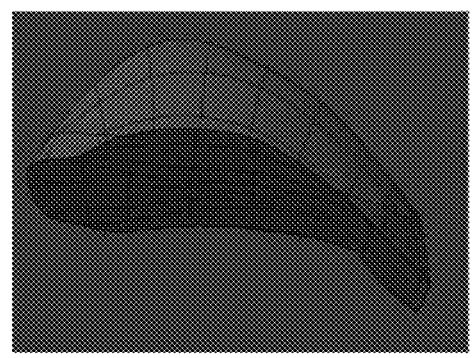

For example, the curved surface of the resected breast part (i.e., the curved surface of the breast prosthesis) may be modeled by applying reverse-design process as shown in FIGS. 4A to 4C.

First, the isoparametric curves are created on the three-dimensional surface model of the horizontally symmetrical normal breast and the user surface of the resected breast part, and a peak is acquired from the three-dimensional surface model of the normal breast so that a plane bordering the peak is created and connected thereto. Then, a 3D curve is created on the user surface of the resected breast part, and then a surface for each of all the points is created and then sketched (see FIG. 4A)

Next, a boundary is created in a three-dimensional curved surface model of the normal breast, and a 3D curved surface model of the non-resected breast is connected to the user surface of the breast resected region using the 3D curve and the sketch created earlier (See FIG. 4B).

Through this process, the curved surface of the resected breast part (i.e., breast prosthesis) as shown in FIG. 4C is modeled.

The step of calculating the volume of the resected breast part (S230) is a step of calculating the volume of the portion surrounded by the curved surface of the modeled resected breast part.

Actually, the breast tissue is classified into two groups: a substantial tissue that consists of a glandular tissue (hereinafter, referred to glandular tissue), and an interstitial tissue that consists of fat (hereinafter, referred to fat tissue). Therefore, in order to manufacture a breast prosthesis that may maintain a balance with normal breast, it is necessary to divide the resected breast part into a glandular tissue dominant layer near a deep part and a fat tissue dominant layer near the body surface and thus calculate the volume and weight of each layer.

A boundary between the glandular tissue dominant layer and the fat tissue dominant layer may be acquired through mammograms acquired by photographing the normal breast, and the curved surface model of the resected breast part is divided into the glandular tissue dominant layer and the fat tissue dominant layer on the basis of the boundary, thereby acquiring the volume of each layer.

Figure 5A:
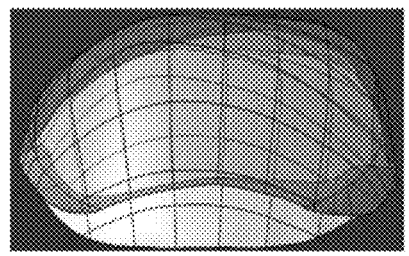
FIGS. 5A to 5C are views illustrating a state in which a glandular tissue dominant layer and a fat tissue dominant layer are separated according to a preferred embodiment of the present invention.
Figure 5B:
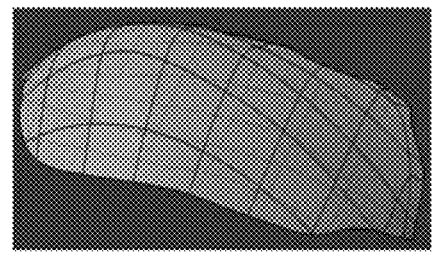
Figure 5C:

For example, in the curved surface model of the resected breast part as shown in FIGS. 5A to 5C, the boundary between the glandular tissue dominant layer and the fat tissue dominant layer is created (see FIG. 5A) to complete the glandular tissue dominant layer (see FIG. 5B), and the glandular tissue dominant layer is removed from the curved surface model of the resected breast part, thereby completing the remaining fat tissue dominant layer (see FIG. 5C).

Then, the volume is calculated using the z-map model for each of the completed glandular tissue dominant layer and fat tissue dominant layer.

In the step of calculating the weight of the resected breast part (S240), the weight of each of the glandular tissue dominant layer and the fat tissue dominant layer is used to calculate volumes of each layer.

Since an intrinsic density of the glandular tissue is above 1 g/mL, and a density of the fat tissue is less than 1 g/mL, so that the density of breast varies depending on the relative distribution ratio between the two tissues. Therefore, densities should be differently applied depending on when calculating the weight of the glandular tissue dominant layer or the weight of the fat tissue dominant layer.

Herein, the weight of the resected breast part can be computed using the regression equation between the volume and the weight of the breast disclosed in the previous studies without directly weighing the resected breast part in the case of a patient with mastectomy (Example: Gurcan Aslan et al. BREAST REDUCTION: WEIGHT VERSUS VOLUME. PLASTIC AND RECONSTRUCTION SURGERY, July 2003).

In addition, there are previous studies that classify types of breasts according to the proportion of total breast occupied by the glandular tissue and thus provide a regression equation between volume and weight for each type (Example: Choi, Kyoung-Wook, Correlation between weight and volume of resected breast tissue in breast cancer mastectomy, Graduate School of Medicine of Yeungnam University 2015).

Therefore, it is possible to calculate the weight of the resected breast part using the regression equation described in these previous studies. Then, the density of each of the glandular tissue dominant layer and the fat tissue dominant layer of the resected breast part may be applied to the volume of each, thereby calculating the target weight of each layer.

Alternatively, for example, the total weight of the resected breast part may be calculated from the total volume using any one of the regression equations of previous studies, and the target weight of the fat tissue dominant layer may be calculated by multiplying the volume of the fat tissue dominant layer by the density of the fat tissue (for example, 0.823 g/cm$^3$). Then, the target weight of the glandular tissue dominant layer may be calculated by subtracting the target weight of the calculated fat tissue dominant layer from the total weight of the resected breast part.

Preferably, the ratio of the fat tissue to the glandular tissue varies from one individual to another, so that the ratio may be determined through the individual's normal breast mammogram to calculate the resected breast part more accurately.

In step S300 of selecting a material of the breast prosthesis, a material of the breast prosthesis that is to be manufactured by the user is selected. For example, silicone, rubber, foam, and the like may be the material of breast prosthesis.

The step of designing the customized breast prosthesis (S400), the breast prosthesis is designed in such a manner as to adjust the target weight of the glandular tissue dominant layer and the target weight of the fat tissue dominant layer with the selected material.

In this step (S400), the breast prosthesis is designed so that inside shapes are applied to each of the glandular tissue dominant layer and the fat tissue dominant layer to adjust the target weight calculated for each layer while maintaining the shape of the glandular tissue dominant layer and the fat tissue dominant layer for the selected material.

For the application of the inside shapes, as shown in Equations 1 and 2, the initial weight of each layer is calculated by multiplying the density of the selected material by the volume of the glandular tissue dominant layer and the volume of the fat tissue dominant layer, respectively, and then a reduction weight or an additional weight is calculated by the difference between the initial weight and the target weight.

$$\Delta W_G = (V_G \times \rho) - W_{TG} \quad \text{[Equation 1]}$$

($W_{TD}$: target weight of glandular tissue dominant layer, $\rho$: material density, $V_G$: volume of glandular tissue dominant layer, $\Delta W_G$: reduction (+) weight or addition (−) weight of glandular tissue dominant layer)

$$\Delta W_F = (V_F \times \rho) - W_{TF} \quad \text{[Equation 2]}$$

($W_{TF}$: target weight of fat tissue dominant layer, $\rho$: material density, $V_F$: volume of fat tissue dominant layer, $\Delta WF$: reduction (+) weight or addition (−+) weight of fat tissue dominant layer)

As inside shapes that may be used to reflect reduction weight or addition weight in the breast prosthesis that is to be made of the material selected by the user, a variety of shapes such as triangular column, square column, bowlegs column, and cylindrical column may be used.

More preferably, the same cylindrical column as the nozzle shape of a typical 3D printer may be precisely removed, and is stable when filling or emptying the inside shapes, making it best suited for the inside shape of the breast prosthesis.

For example, when the weight of the inside shape is to be reduced, the inside shapes are formed of voids. On the other hand, when the weight of the inside shape is to be added, the inside shape is formed with a material having a higher density than the density of material of the breast prosthesis.

Figure 6:
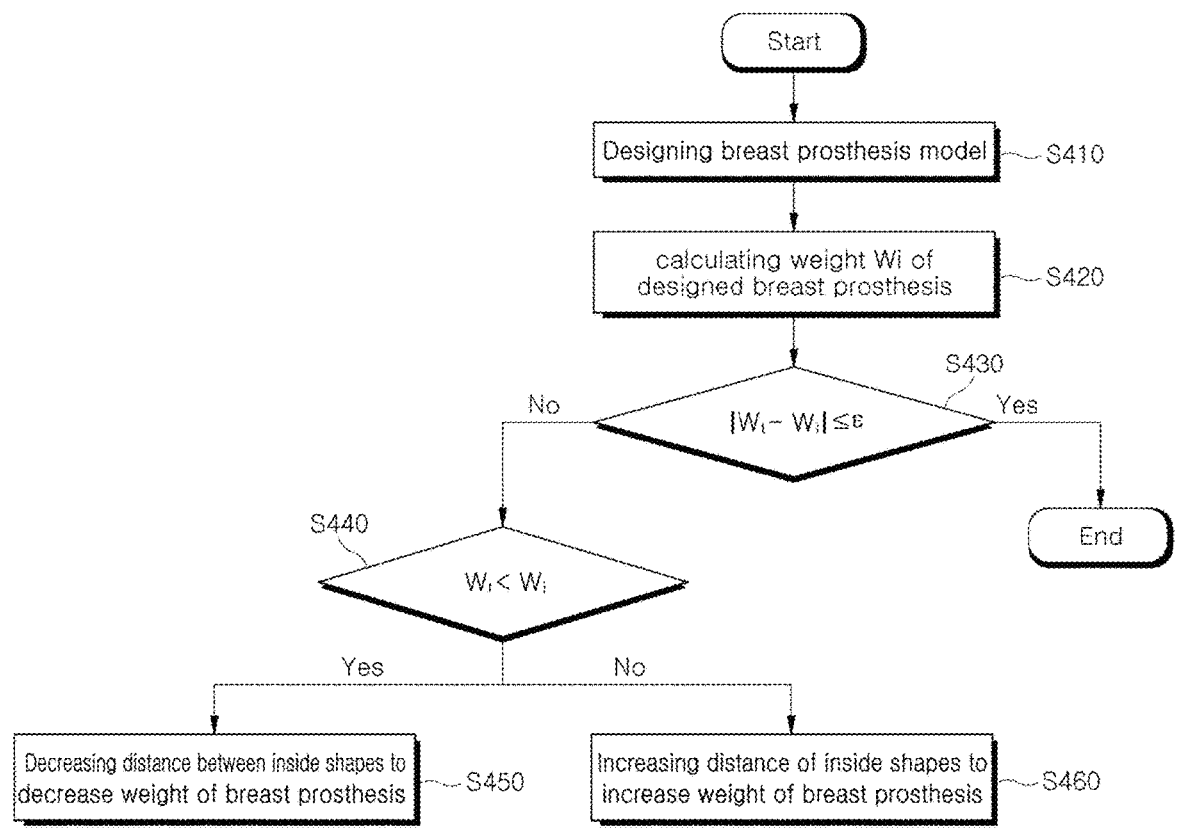
FIG. 6 shows a detailed flow diagram of a step of designing a customized breast prosthesis in which internal shapes are formed of voids according to a preferred embodiment of the present invention.

FIG. 6 shows a detailed flow diagram of the step of designing a customized breast prosthesis in which inside shapes are formed of voids according to a preferred embodiment of the present invention. That is, the present embodiment corresponds to the case where the material density of the breast prosthesis is higher than the density of the actual breast tissue, and thus the weight reduction is required.

As shown in FIG. 6, step of designing a customized breast prosthesis (S400) includes steps of designing a breast prosthesis (S410), calculating the weight Wi of the designed breast prosthesis (S420), determining whether or not a difference between the target weight Wt and the designed breast prosthesis weight Wi is within an allowable tolerance (S430), comparing the target weight Wt with the designed breast prosthesis weight Wi (S440), and decreasing the distance between the inside shapes to decrease the weight of the breast prosthesis (S450) or increasing the distance of the inside shapes to increase the weight of the breast prosthesis (S460).

Here, the step of designing the customized breast prosthesis (S400) may be applied to each of the glandular tissue dominant layer and the fat tissue dominant layer.

In the step of designing the breast prosthesis (S410), first, the user sets variables such as a guideline for applying inside shapes to each of the glandular tissue dominant layer and the fat tissue dominant layer of the breast prosthesis, a type of an inside shape (for example, cylindrical column), a center point of the inside shape, the cross-sectional length of the inside shape (for example, the diameter of the cylindrical column), the distance between the inside shapes, the number of the inside shapes, and the like and designates values thereto.

For example, when a cylindrical column is applied as an inside shape, the variables for each of the glandular tissue dominant layer and the fat tissue dominant layer of the breast prosthesis are set and the values thereof are designated as follows.

First, the vertical and horizontal guideline (M_Box) of the breast prosthesis is set to apply a constraint condition to the cylindrical column pattern. Then, the center of the circle (Dot) in the cylindrical column is set. The center of the circle (Dot) is a variable that serves not to get out of the guide line (M_Box) of the constraint condition when changing the distance between the cylindrical columns and the diameter thereof, and the value thereof is set using equation 3 below.

$$\text{Dot} = (M\_Box - ((M\_Box \div \text{Distance}) - 1 \text{ mm}) \times \text{Distance}) \div 2 \text{ mm} \quad \text{[Equation 3]}$$

Then, the circle diameter (Circle_w) of the inside shape is set and the distance between the inside shapes (Distance) is set.

A number variance (pattern instance) of inside shape patterns is set, and the number of patterns is controlled using equation 4 below so as not to deviate from the guide line (M_Box).

$$\text{Pattern Instance} = M\_Box \div \text{Distance} \quad \text{[Equation 4]}$$

(Where, a value of pattern instance is an integer.)

Then, setting is performed to design the skin tissue in the breast taken using a mammogram and the like. For example, the setting may be performed with 3 mm offset in an −y direction at the breast's highest point.

Then, the inside shapes are designed by setting the variable values for each of the glandular tissue dominant layer and the fat tissue dominant layer of the breast prosthesis (see FIG. 7A1 and FIG. 7A2, and then intersected with the glandular tissue dominant layer (see FIG. 7B) and the fat tissue dominant layer (see FIG. 2B2), respectively, thereby designing inside models of the breast prosthesis (see FIG. 7C1 and FIG. 7C2). In this case, the fat tissue dominant layer is intersected using the part offset by the skin tissue.

Finally, the breast prosthesis is designed by overlapping the intersected inside shape part with the glandular tissue dominant layer and the fat tissue dominant layer that are not offset by the skin tissue (see FIG. 7D1 and FIG. 7D2).

The step S420 of calculating the weight of the designed breast prosthesis is performed by deleting the weight of the intersected inside shape part from the weight calculated by multiplying the density of the selected material by the volume of the breast prosthesis. Here, the weight of the intersected inside shape part is calculated by multiplying the volume of the intersected inside shape part by the density of the breast prosthesis material.

In the step of determining whether or not a difference between the target weight $W_t$ and the designed breast prosthesis weight $W_i$ is within an allowable tolerance (S430), it is determined whether the difference between the target weight and the designed breast prosthesis is within a predetermined allowable tolerance. When the difference is within the allowable tolerance, the step of designing the customized breast prosthesis (S400) is terminated.

However, when the difference between the target weight $W_t$ and the designed breast prosthesis weight $W_i$ exceeds the allowable tolerance ε, the target weight $W_t$ and the designed breast prosthesis weight $W_i$ are compared with each other.

When the target weight $W_t$ is less than the weight of the designed breast prosthesis $W_i$, the weight of the breast prosthesis is reduced by reducing the distance between the inside shapes (S450) (see FIGS. 8A and 8B).

When the target weight $W_t$ is greater than the designed breast prosthesis weight $W_i$, the weight of the breast prosthesis is increased by increasing the distance between the inside shapes (S460) (see FIG. 9A->FIG. 9B1).

In the case of the customized breast prostheses (i.e., the inside shapes are formed of voids) that are designed by reducing most weight, the target weight may be adjusted by increasing the distance between the inside shapes.

However, when it is not possible to exceptionally adjust the weight, the inner shapes are filled with high-density material to increase the weight of the breast prosthesis (see FIG. 9A->FIG. 9B2). In addition, when the weight of the breast prosthesis is too light to have a large difference from the target weight, the weight of the breast prosthesis is increased by inserting a heavy object into the glandular tissue dominant layer (see FIG. 9A->FIG. 9B3)

From the step of designing the breast prosthesis (S450) to the step of reducing the weight of the breast prosthesis by reducing the distance of the inside shapes (S450) or the step of increasing the weight of the breast prosthesis by increasing the distance of the inside shapes (S460) are repeated until the difference between the target weight $W_t$ and the designed breast prosthesis weight $W_i$ is within the allowable tolerance, and are terminated as soon as the tolerance is within the tolerance.

Figure 10:
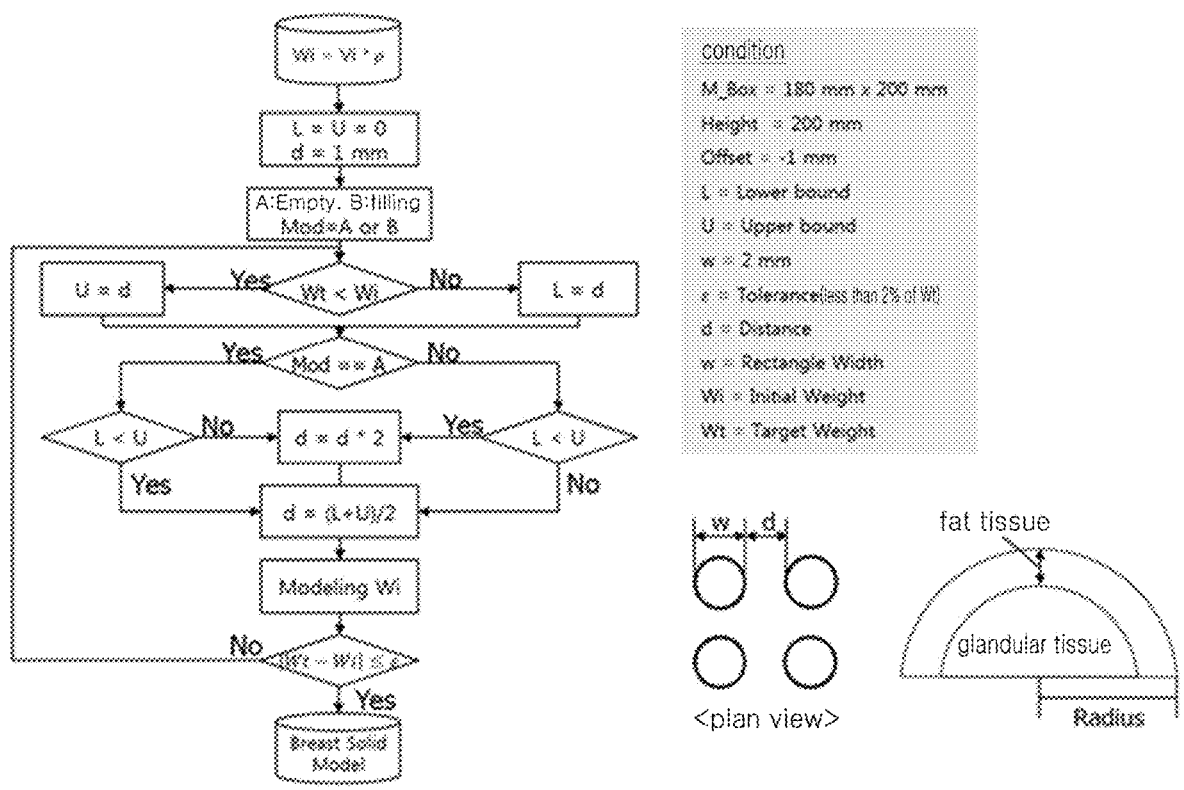
FIG. 10 is a flowchart of a binary search algorithm for designing a customized breast prosthesis in which inside shapes are formed of voids according to a preferred embodiment of the present invention.

FIG. 10 is a flowchart of a binary search algorithm for designing the customized breast prosthesis in which inside shapes are formed of voids according to a preferred embodiment of the present invention. That is, the present embodiment corresponds to the case where the density of the material of the breast prosthesis is higher than the density of the actual breast tissue, and thus the weight reduction is required.

Referring to FIG. 10, the algorithm is used in such a manner that an initial d value is designated as a variable, and variables of a lower bound and an upper bound are created, so that the target weight and the designed breast prosthesis weight are compared to search for an intermediate value thereof. When the target weight is less than 2% of the error range according to the d value that changes all the time, the algorithm cycle is immediately terminated and the final designed breast prosthesis may be saved as a breast solid model.

The binary search algorithm of FIG. 10 may also be applied to each of the glandular tissue dominant layer and the fat tissue dominant layer of breast prosthesis.

In the case of FIGS. 6 to 10 above-mentioned, the density of the breast prosthesis material is larger than that of the actual breast tissue so that the inside shapes are formed of voids. However, even in the case that the density of the breast prosthesis is smaller than that of the actual breast tissue so that the inside shapes are formed of a material having a density higher than that of the material of the breast prosthesis, it is possible to provide the customized breast prosthesis in which the target weight is adjusted within an allowable error by adjusting the distance between the inside shapes.

The step of performing three-dimensional printing of the customized breast prosthesis (S500) is a step of printing the breast prosthesis finally designed with a material selected by the user (for example, TangoPlus FLX390) using a 3D printer 13 such as a 3D printer. In this case, the breast prosthesis may be divided into the glandular tissue dominant layer and the fat tissue dominant layer, which may be printed respectively.

Figure 11A:
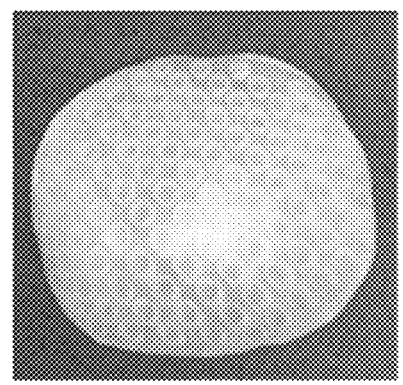
FIGS. 11A and 11B are views illustrating a 3D-printed breast prosthesis according to a preferred embodiment of the present invention.
Figure 11B:
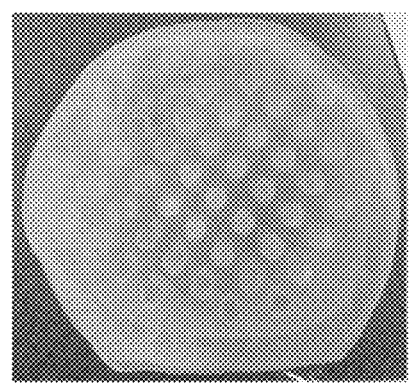

FIGS. 11A and 11B are views illustrating a 3D-printed breast prosthesis according to a preferred embodiment of the present invention. As shown in FIGS. 11A and 11B, it is preferable that the inner structure is designed with a certain offset so that openings due to the inside shapes is not formed on the upper surface (FIG. 11A) and the lower surface (FIG. 11B) of the breast prosthesis. When the design is performed with a certain offset, it is possible to prevent inconvenience from being caused to a user due to a sharp portion and prevent foreign matter such as dust from accumulating inside.

In another embodiment, the present invention provides a manufacturing system 10 that performs a method of manufacturing the customized breast prosthesis as described above.

In yet another embodiment, the present invention provides a computer program stored on a computer readable recording medium to execute the method of manufacturing the customized breast prosthesis as described above, and such computer readable recording medium may include a CD-ROM, USB memory, and the like.

In yet another embodiment, the present invention provides a customized breast prosthesis manufactured by the method of manufacturing the customized breast prosthesis as described above.

In yet another embodiment, the present invention provides a customized brassiere manufactured on the basis of creational design pattern using three-dimensional scanned data of a user's body in order to accommodate the customized breast prosthesis as described above.

The pattern of the customized brassiere may be manufactured as follows.

First, a user's body is scanned with a three-dimensional scanning device, and a baseline and a design line are set using the scanned data. Then, the panel is separated according to the design line and stored, and then a flattening operation that converts the resulting into a two-dimensional pattern is performed. Then, vertices and lines of the two-dimensional pattern are connected and outlines are arranged. Finally, the design line is modified through a three-dimensional virtual fitting that allows the flattened brassiere pattern to be virtually tried on the user's three-dimensional scan data.

Figure 12A:
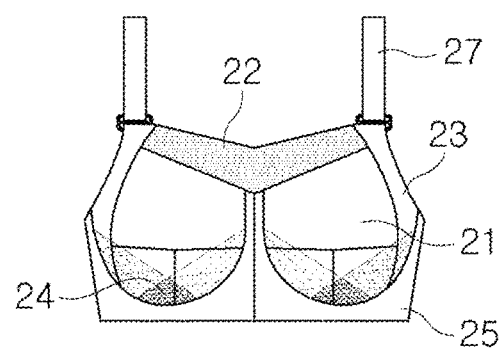
FIGS. 12A and 12B are views showing a customized correction brassiere according to a preferred embodiment of the present invention.
Figure 12B:
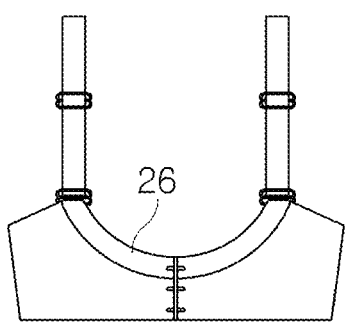

An example of a customized correction brassiere manufactured using this pattern is shown in FIGS. 12A and 12B.

Referring to FIGS. 12A (front view) and 12B (rear view), the customized brassiere 20 for accommodating the above-mentioned customized breast prosthesis includes a patch type cup 21 having a top cup and a bottom cup separated from each other, an upper extension 22 of mesh material extended to an upper edge of the top cup, a left and right extension 23 extended to both sides of the patch type cup, a support 24 formed with a panel of a stretchable material positioned inside the patch type cup, an under portion 25 connected to a lower portion of the patch type cup and having a lower side tape of a prescribed height or more, a U-shaped wing 26 connected to left and right sides of the under portion, and a shoulder strap 27 connected to the U-shaped wing and having a prescribed width or more.

The patch type cup 21 is divided into a top cup and a bottom cup to provide a natural breast line and a breast correction effect.

The upper extension 22 is formed of a mesh material to provide permeability to the breast part.

The left and right extension 23 is provided such that the original material of the brassiere is extended to left and right sides of the patch type cup 21 to provide a tight-fitting brassiere and to pull the breasts together.

The support 24 may be formed with a stretchable material capable of replacing the wire, so that the breasts may be pulled together and a tight-fitting brassiere may be provided without causing breast pain and inconvenience due to the wire.

The under portion 25 is provided with a lower edge tape of a prescribed height (for example, 2 cm) or more to prevent the brassiere from being raised during the activity.

The U-shaped wing 26 is larger in area than the straight wing, and thus is effective in compensating extra flab.

The shoulder strap 27 is formed to have a prescribed width (for example, 2 cm) or more so as to disperse a feeling of pressure applied upon the shoulder. In addition, the length thereof may be adjusted according to the user's body size.

The invention claimed is:

1. A method of manufacturing a customized breast prosthesis performed by a system for manufacturing the customized breast prosthesis, the method, comprising:
    performing three-dimensional scanning of a user's body;
    acquiring shape, volume, and weight data of a resected breast part;
    selecting a material of the breast prosthesis;
    designing the customized breast prosthesis that is adjusted to the shape, volume, and weight of the resected breast part with the selected material of the breast prosthesis,
    wherein the acquiring of the shape, volume, and weight data of the resected breast part includes determining whether the shape, volume, and weight data of the resected breast part are acquired or not,
    and when the shape, volume, and weight data of the resected breast part are not acquired, further includes:
    modeling a curved surface of the resected breast part;
    calculating the volume of the resected breast part using the curved surface of the modeled resected breast part; and
    calculating the weight of the resected breast part from the volume of the resected breast part,
    wherein the modeling of the curved surface of the resected breast part includes:
    modeling a curved surface of a normal breast part form the scanned data;
    moving the modeled curved surface of the normal breast part in a horizontally symmetrical manner on the basis of a breast center line; and
    modeling the curved surface of the resected breast part by connecting the normal breast part moved in the horizontally symmetrical manner to a user surface of a breast resected region.

2. A method of manufacturing a customized breast prosthesis performed by a system for manufacturing the customized breast prosthesis, the method, comprising:
    performing three-dimensional scanning of a user's body;
    acquiring shape, volume, and weight data of a resected breast part;
    selecting a material of the breast prosthesis;
    designing the customized breast prosthesis that is adjusted to the shape, volume, and weight of the resected breast part with the selected material of the breast prosthesis,
    wherein the acquiring of the shape, volume, and weight data of the resected breast part includes determining whether the shape, volume, and weight data of the resected breast part are acquired or not,
    and when the shape, volume, and weight data of the resected breast part are not acquired, further includes:
    modeling a curved surface of the resected breast part;
    calculating the volume of the resected breast part using the curved surface of the modeled resected breast part; and
    calculating the weight of the resected breast part from the volume of the resected breast part,
    wherein the calculating of the volume of the resected breast part includes:
    creating a boundary of a glandular tissue dominant layer and a fat tissue dominant layer in the curved surface model of the resected breast part to complete the glandular tissue dominant layer;
    removing the glandular tissue dominant layer from the curved surface model of the resected breast part to complete the fat tissue dominant layer; and
    calculating each of a volume of the glandular tissue dominant layer and a volume of the fat tissue dominant layer.

3. The method of claim 2, wherein the calculating of the volume of the resected breast part includes:
    calculating the weight of the resected breast part from a regression equation between a volume and a weight of the breast;
    calculating a target weight of the glandular tissue dominant layer using a volume of the glandular tissue dominant layer and a density of glandular tissue, or calculating a target weight of the fat tissue dominant layer using a volume of the fat tissue dominant layer and a density of fat tissue;
    calculating the target weight of the fat tissue dominant layer by subtracting the target weight of the glandular tissue dominant layer from the weight of the resected breast part, or calculating the target weight of the glandular tissue dominant layer by subtracting the target weight of the fat tissue dominant layer from the weight of the resected breast part.

4. The method of claim 3, wherein the designing of the customized breast prosthesis is performed by applying inside shapes to each of the glandular tissue dominant layer and the fat tissue dominant layer to adjust the target weight of the glandular tissue dominant layer and the target weight of the fat tissue dominant layer while maintaining a form of each of the glandular tissue dominant layer and the fat tissue dominant layer with the selected material.

5. The method of claim 4, wherein for the application of the inside shapes, a reduction weight or an addition weight of the glandular tissue dominant layer is calculated using an equation below to adjust the target weight of the glandular tissue dominant layer, $$\Delta W_G = V_G \times \rho) - W_{TG}$$

($W_{TG}$: target weight of glandular tissue dominant layer, ρ: material density, $V_G$: volume of glandular tissue dominant layer, $\Delta W_G$: reduction (+) weight or addition (−) weight of glandular tissue dominant layer), and a reduction weight or an addition weight of the fat tissue dominant layer is calculated using an equation below to adjust the target weight of the fat tissue dominant layer, $$\Delta W_F = (V_F \times \rho) - W_{TF}$$

($W_{TF}$: target weight of fat tissue dominant layer, ρ: material density, $V_F$: volume of fat tissue dominant layer, ΔWF: reduction (+) weight or addition (−) weight of fat tissue dominant layer).

6. The method of claim 5, wherein the breast prosthesis is designed by forming the inside shapes with voids when it is necessary to reduce the weight to adjust the target weight for each layer, and the breast prosthesis is designed by forming the inside shapes with a material having a density higher than that of a material of the breast prosthesis when it is necessary to add the weight to adjust the target weight.

7. The method of claim 6, wherein a distance between the inside shapes is adjusted to adjust the target weight until a difference between the designed breast prosthesis weight and the target weight is within an allowable tolerance.

8. The method of claim 1, further comprising:
performing 3D printing of the designed customized breast prosthesis upon the selected material of the breast prosthesis.

9. A customized breast prosthesis manufactured by the method according to claim 1.

10. A customized correction brassiere manufactured on the basis of creational design pattern using three-dimensional scanned data of a user's body to accommodate the customized breast prosthesis of claim 9, the brassiere comprising:
a patch type cup having a top cup and a bottom cup separated from each other;
an upper extension of mesh material extended to an upper edge of the top cup;
a left and right extension extended to both sides of the patch type cup;
a support formed with a panel of a stretchable material positioned inside the patch type cup;
an under portion connected to a lower portion of the patch type cup and having a lower side tape of a height of 2 cm or more;
a U-shaped wing connected to left and right sides of the under portion; and
a shoulder patch connected to the U-shaped wing and having a width of 2 cm or more.

11. A computer program stored on a computer readable recording medium to execute the method according to claim 1.

12. A computer readable recording medium storing the computer program of claim 11.

\* \* \* \* \*